United States Patent
Nakousi et al.

(10) Patent No.: US 7,005,083 B2
(45) Date of Patent: Feb. 28, 2006

(54) PROCESS FOR THE PREPARATION OF ALKYLLITHIUM COMPOUNDS

(75) Inventors: Carlos F. Nakousi, Las Condes (CL); Thomas R. Currin, Jr., Salisbury, NC (US)

(73) Assignee: SQM Lithium Specialties Limited Partnership, LLP, Atlanta, GA (US)

( * ) Notice: Subject to any disclaimer, the term of this patent is extended or adjusted under 35 U.S.C. 154(b) by 125 days.

(21) Appl. No.: 10/343,473

(22) PCT Filed: Aug. 8, 2001

(86) PCT No.: PCT/US01/24830

§ 371 (c)(1),
(2), (4) Date: Jul. 7, 2003

(87) PCT Pub. No.: WO02/12150

PCT Pub. Date: Feb. 14, 2002

(65) Prior Publication Data

US 2004/0251562 A1 Dec. 16, 2004

Related U.S. Application Data

(60) Provisional application No. 60/223,714, filed on Aug. 8, 2000.

(51) Int. Cl.
*C02F 1/02* (2006.01)
*C09K 3/00* (2006.01)

(52) U.S. Cl. .............................. 252/182.3; 252/182.12; 252/182.14; 260/665 R

(58) Field of Classification Search ............. 260/665 R
See application file for complete search history.

(56) References Cited

U.S. PATENT DOCUMENTS

| | | | |
|---|---|---|---|
| 2,947,793 A | 8/1960 | Eberly | |
| 3,122,592 A | 2/1964 | Eberly | |
| 3,293,313 A | 12/1966 | Borkowski | |
| 3,420,903 A | 1/1969 | Smith | |
| 3,452,112 A | 6/1969 | Kamienski | |
| 4,976,886 A | 12/1990 | Morrison et al. | |
| 5,141,667 A | 8/1992 | Morrison et al. | |
| 5,211,887 A | 5/1993 | Morrison et al. | |
| 5,211,888 A | 5/1993 | Morrison et al. | |
| 5,332,533 A | 7/1994 | Schwindeman et al. | |
| 5,340,507 A | 8/1994 | Morrison et al. | |
| 5,523,447 A | 6/1996 | Kamienski et al. | |
| 5,626,798 A | 5/1997 | Schwindeman et al. | |
| 5,663,398 A | 9/1997 | Schwindeman et al. | |
| 5,776,369 A | 7/1998 | Dover et al. | |
| 5,827,929 A | 10/1998 | Schwindeman et al. | |

OTHER PUBLICATIONS

CA:92:22539 abs of J Prakt Chem by Giancaspro et al 321(5) pp 876–7 1979.*
Beel et al., 1959, "Effect of Sodium in the Preparation of n–Butyllithium," *J. Org. Chem.* 24(2):2036–38.
Guo et al., 1985, "α–Deuterium and Carbon–13 Kinetic Isotope Effects Associated with the $S_N2$ Displacement of Iodide and Tosylate by Lithium Organocuprates," *J. Am. Chem. Soc.* 107(21):6028–30.
Stiles et al., 1959, "Rearrangement of Alkyl Groups. Kinetic and Tracer Studies in the Pinacol Rearrangements," *J. Am. Chem. Soc.* 81(6):1497–1503.
Giancaspro et al., "A simple procedure for preparing tert–butyllithium in reproducible high yields", J. Prakt. Chem 1979, pp. 876–877.
Molle et al., "Cage structure organometallic Compounds: 1–Diamantyle, 1–twistyl, 1–triptycyl and 2–adamantyl lithium compounds", Tetrahderon Lett. (34), 1978, pp. 3177–3180s.

* cited by examiner

*Primary Examiner*—Johann Richter
*Assistant Examiner*—Chukwuma Nwaonicha
(74) *Attorney, Agent, or Firm*—Jones Day

(57) ABSTRACT

A process for preparing alkyllithium compounds by reacting a sodium-lithium alloy with alkyl halides at temperatures of about 50 to 125° C.

19 Claims, No Drawings

PROCESS FOR THE PREPARATION OF ALKYLLITHIUM COMPOUNDS

This application claims the benefit of U.S. provisional application No. 60/223,714, filed Aug. 8, 2000, and International Application no. PCT/US01/24830, filed Aug. 8, 2001, the disclosure of each application being incorporated by reference herein in its entirety.

FIELD OF THE INVENTION

The present invention is directed to a high temperature process for preparing alkyllithium compounds containing 2 to 16 carbon atoms by reacting a sodium-lithium alloy with alkyl halides at temperatures of 50 to 125° C.

BACKGROUND OF THE INVENTION

Methods of preparation of hydrocarbon derivatives of lithium compounds have been published by various workers in the field, such as, for example, K. E. Eberly, U.S. Pat. No. 2,947,793, which issued Aug. 2, 1960, which patent teaches a process for preparation of alkylene dilithium compounds.

Eberly, in U.S. Pat. No. 3,122,592, discloses a method for the preparation of alkyl lithium compounds which involves reacting a monohaloalkane comprising 3 to 8 carbon atoms with finely divided particles of an alloy consisting of lithium and from 0.3 to 1.0 percent sodium or potassium, the reaction being effected at a temperature of from 0–60° C. Eberly discloses that the yield of carbon-bonded lithium increases to a maximum of 87.89 percent at a corresponding level of 0.36 percent sodium alloyed in lithium. A drawback to the process is that the reaction is slow, with the addition of monohaloalkane requiring up to several hours, followed by additional time to allow the reaction to become complete and potentially several hours standing time to allow separation of products and by-products.

A process for producing alkyllithium containing six or more carbon atoms, such as octyllithium is disclosed by C. Guo and coworkers, J. Am. Chem. Soc., 1985, 107, 6030 who employed a refluxing hexane medium and a four hour post addition reflux to obtain a yield of about 70%.

Similarly, U.S. Pat. No. 3,452,112 to Kamienski et al. discloses a method of preparing organic solvent solutions of lithium-hydrocarbon compounds which comprises adding a preformed alkyl lithium compound to a dispersion of finely divided lithium in a non-reactive liquid medium, and subsequently adding to this mixture an unsaturated hydrocarbon or a hydrocarbon halide which is reactive with lithium to produce the desired product. Kamienski further discloses that the reaction is carried out at a temperature of between −50 to 5 ° C., and that the lithium metal used be essentially pure or commercially available material, employing a small amount of sodium metal of about 0.25 to about 1 weight percent based on the lithium metal. The patent discloses, however, that the addition of the reactants and the time taken to bring the reaction to completion could take several hours.

High purity concentrated alkyllithium solutions are highly desirable as it is important that the alkyllithium product be free from or at least low in olefin content as olefins lead to the development of deep yellow colored alkyllithium products. The level of chloride ion impurities is important as high chloride values of 300 ppm and above generally result in hazy alkyllithium products. While concentrated, clear solutions of alkyllithium compounds in hydrocarbon solvents are clearly desirable, they are difficult to obtain. One reason for this is that concentrated solutions of alkyllithium compounds are highly viscous so that unreacted excess lithium generally employed in the reaction is difficult to remove by filtration or other conventional particle separation means. The prior art processes produce alkyllithium compounds containing over 300 parts per million of dissolved inorganic halides, including, inter alia, lithium chloride, which are not removed by filtration. When the resulting product-containing solutions are concentrated by distillation or other solvent removal means, by-products such as lithium halide form fine crystals in the product solution. This leads to a hazy appearance in the product, and is generally undesirable in industrial processes. Further, the halide by-products mat actually precipitate out of solution, resulting in an even more undesirable product. Thus, a process which leads to the production of alkyllithium compounds in high yields of 90% or better, are highly desirable economically.

U.S. Pat. No. 3,452,112, discussed above, results in product alkyllithium solutions in yields lower than 85 percent. Unsaturated hydrocarbon-lithium adducts are produced in higher yields, but are colored solutions.

U.S. Pat. No. 5,332,533 discloses a process for producing alkyllithium by reacting a primary alkyl halide with lithium metal in a liquid hydrocarbon solvent in an inert atmosphere at a temperature between 35 and 125 degrees centigrade. This process, however, also requires an extended feed time followed by further time to bring the reaction to completion. Further, the products of the reactions are generally solutions having a yellow color. Therefore, a need remains for a process for preparation of clear, colorless solutions of alkyllithium compounds which forms such products in high yield and high purity and in shorter reaction times. The present invention overcomes the disadvantages of the prior art and provides a process that satisfies this need.

SUMMARY OF THE INVENTION

The present invention is directed to an improvement in the process for producing alkyllithium compounds in high yields of about 90 percent and high purity by reacting under reflux conditions in a liquid hydrocarbon solvent which refluxes at temperatures between about 50° C. and 125° C., such solvent being selected from liquid saturated aliphatic hydrocarbons containing 5 to 12 carbon atoms, saturated liquid cycloaliphatic hydrocarbons containing 5 to 12 carbon atoms and liquid aromatic hydrocarbons containing 6 to 12 carbon atoms and mixtures thereof, an alkyl halide containing 3 to 16 carbon atoms with metal particles of less than 300 microns in size, and subsequently recovering the alkyllithium compound, in which the improvement consists of conducting the reaction using metal particles of a lithium-sodium alloy which comprises greater than about 1 percent by weight sodium.

DETAILED DESCRIPTION OF THE INVENTION

The present invention is directed to a process for an improvement in the process for producing alkyllithium compounds in high yields of about 90% and high purity by reacting under reflux conditions in a liquid hydrocarbon solvent which refluxes at temperatures between about 50° C. and 125° C., such solvent being selected from liquid saturated aliphatic hydrocarbons containing 5 to 12 carbon atoms, saturated liquid cycloaliphatic hydrocarbons containing 5 to 12 carbon atoms and liquid aromatic hydrocarbons containing 6 to 12 carbon atoms and mixtures thereof, an alkyl halide containing 3 to 16 carbon atoms with metal particles of less than 300 microns in size, and subsequently recovering the alkyllithium compound, in which the improvement consists of conducting the reaction using metal particles of a lithium-sodium alloy which comprises greater than about 1 percent by weight sodium.

Solid sodium metal and solid lithium metal are dispersed in a hydrocarbon liquid medium under conditions sufficient to form a sodium-lithium alloy dispersion. The dispersion is prepared in a pressure reactor fitted with an agitator. Amounts of sodium and lithium sufficient to produce the desired sodium: lithium ratio are added to the reactor, followed by a sufficient amount of hydrocarbon liquid medium and dispersing agent. The reactor is then heated and the metals are alloyed under agitation at the melting point of lithium metal. The sodium: lithium alloy dispersion is then allowed to cool to about 100° C.

The sodium-lithium alloy is typically composed of a ratio of between 1–50% by weight sodium and 99–50% by weight lithium. Preferably the sodium-lithium alloy is composed of about 30% by weight sodium and about 70% by weight lithium. The sodium-lithium alloy is commercially available as a dispersion from Postin Products, Inc. (Faith, N.C.).

The sodium-lithium alloy is added to a reactor vessel. Excess sodium-lithium alloy in amounts of up to 7% by weight above stoichiometric amounts are used to insure reaction of all the alkyl chloride. Alkyl halide and at least one hydrocarbon liquid solvent are added, and the reaction in which alkyllithium is formed is carried out under reflux at a temperature which is equal to or greater than the boiling point of the hydrocarbon liquid solvent. Generally the reaction is carried out at a temperature up to about 10° C. above the boiling point of the hydrocarbon liquid solvent. The preferred hydrocarbon liquid solvent is hexane, and the reaction is preferably carried out at about 71–81 ° C.

Insoluble materials such as unreacted lithium metal, unreacted sodium metal, lithium chloride and sodium chloride are removed by filtration. The filter cake, containing such insoluble materials, is washed with reaction solvent to remove any residual alkyllithium product. The alkyllithium product and the solvent washes are collected in a product tank.

The unreacted lithium metal, unreacted sodium metal, lithium chloride and sodium chloride are recovered as lithium metal and sodium metal. The remaining solvent is recovered by distillation.

Suitable alkyl halides for use in the process of the invention contain 2 to 16 carbon atoms and the halide ion may be bromo, chloro or iodo with chloro being preferred as being less expensive and more generally available.

Hydrocarbon liquids suitable for use in the process of this invention include light mineral oil, liquid saturated aliphatic and cycloaliphatic hydrocarbons containing 5 to 12 carbon atoms such as isopentane, n-pentane, n-hexane, n-heptane, 2-ethylhexane, iso-octane, n-octane, decane, dodecane and the like or saturated cyclic hydrocarbons containing 5 to 12 carbon atoms such as cyclopentane or methylcyclohexane and the like and mixtures thereof. Aromatic hydrocarbons containing 6 to 12 carbon atoms such as benzene, toluene, n-propyl benzene, isopropylbenzene, xylenes, 1,2,3,4-tetrahydronaphthalene and the like may also be used. Since reflux conditions and optimum reaction temperatures are related, hydrocarbon mixtures are quite useful. Nevertheless, a single liquid hydrocarbon may be more desirable than mixed hydrocarbons.

Suitable dispersing agents include fatty acids, alcohols and esters. Particularly suitable dispersing agents include lauric acid, myristic acid, palmitic acid, linoleic acid, linolenic acid, oleic acid, stearic acid and derivatives and mixtures thereof The reaction may be effected at temperatures from about 50–125° C., with optimum results being obtained at a temperature equal to or up to about ten degrees greater than the boiling point of the solvent or solvent mixture. The reaction may be brought about at temperatures lower than the boiling point of the solvent, however, poorer results are obtained compared to those achieved under reflux conditions.

Generally, the reaction is effected by introducing the sodium: lithium alloy dispersion into the reactor. Dispersion hydrocarbon medium liquid is then replaced by the desired reaction solvent, if necessary. The reactor is heated and agitation is applied. Alkyl halide and solvent is added to the agitated dispersion. The reactor is heated to the reflux temperature the reactor is heated to a temperature equal to or up to about ten degrees greater than the boiling point of the solvent or solvent mixture, and alkyl halide and solvent is added at a rate so that the addition is completed in approximately one hour. Once the addition is completed, agitation is maintained for a further period of about ten minutes. The reaction media should be cooled or allowed to cool to ambient conditions once the reaction is completed.

Experiments were conducted employing various sodium-lithium alloy percentage compositions and commercially available alkyl chlorides and solvents. The sodium-lithium alloy dispersion was added to the selected solvent in a reactor equipped with a reflux condenser, a stirrer, a feed device for adding the alkyl chloride and means for heating the reactor and reaction mass. The sodium-lithium-solvent mixture was stirred and heated to the selected reaction temperature, often the boiling point or ten degrees above the boiling point of the selected solvent, and the alkyl chloride feed was started. Thereafter, the temperature was controlled by the rate of alkyl chloride addition. Process variables such as reaction temperatures, halide feed rate, excess sodium-lithium alloy and the effect these variables have on yield and purity were extensively studied.

The invention will now be illustrated by the following examples. The examples are not intended to be limiting of the scope of the present invention. In conjunction with the general and detailed descriptions above, the examples provide further understanding of the present invention.

EXAMPLES

Preparation of Butyllithium

Several experiments were conducted to prepare butyllithium. Four different alloys of sodium: lithium were utilized. The sodium: lithium alloys used were obtained as dispersions from Postin Products, Inc. The alloys were as follows:

66% Li/34% Na

50% Li/50% Na

85% Li/15% Na

99% Li/1% Na

Each alloy was reacted with butyl chloride using hexane as solvent. The 66% Li/34% Na alloy was also reacted with butyl chloride in three separate runs using cyclohexane, heptane and toluene as solvents.

The reaction time for each run was 70 minutes.

Butyllithium reactions were run with the prepared sodium: lithium alloy dispersions using the solvents under evaluation and the four different Li/Na concentrations.

A 500 ml. glass agitated flask with a reflux condenser was used for the Butyllithium reflux reactions. 68 grams of n-butyl chloride and 60 ml of hexane were used for the reaction with 14.5 grams of 66% Li/34% Na alloy dispersed in hexane. For the other Li/Na concentrations these amounts were adjusted based on the amount of lithium metal by ratio, and the hexane replaced with the required solvent.

The reaction flask was loaded with the correct dispersion/solvent in the Argon glove box. The reaction flask was transferred to the hood and the reaction apparatus assembled. The reaction apparatus entails the agitator, Argon, BuCl/Solvent feed funnel, reflux condenser and condenser cooling fluid supply and return. The solvent and butyl chloride were added to a glass funnel. The reaction flask agitator was started. Butyl chloride and solvent were slowly added to the agitated dispersion. The apparatus was heated until reflux conditions were achieved, and butyl chloride added. The addition of butyl chloride took approximately one hour, with the reaction initiating instantaneously. The reaction mixture was agitated for a further 10 minutes and then allowed to cool to room temperature.

Following the reaction, the resulting reaction products were washed and filtered with solvent. A 500 ml glass frit filter and 200 ml of solvent was used for the filtration. The contents of the reaction flask were transferred to the filter apparatus under pressure. The filter was pressurized with nitrogen. The reaction "muds" were rinsed three times with equal portions of solvent. Butyllithium product and solvent were collected for analysis and the "muds" collected for recovery. The butyllithium solution was analyzed for active butyllithium and residual lithium. No filter aid was required to assist in filtration of the reaction products.

| Batch # | Na/Li ratio | Reaction Temp. C. | wt. BuLi grams | % yield | Clarity/Color |
|---|---|---|---|---|---|
| 1 | 34/66 | 68 | 4,212 | 90.1 | Clear |
| 2 | 34/66 | 68 | 4,212 | 90.1 | Clear |
| 3 | 34/66 | 68 | 4,237 | 90.6 | Clear |
| 4 | 34/66 | 68 | 4,212 | 90.1 | Clear |
| 5 | 34/66 | 68 | 4,419 | 94.5 | Clear |
| 6 | 15/85 | 68 | 4,405 | 94.2 | Clear |
| 7 | 15/85 | 68 | 4,243 | 90.7 | Clear |
| 8 | 15/85 | 68 | 4,307 | 92.1 | Clear |
| 9 | 15/85 | 68 | 4,316 | 92.3 | Clear |
| 10 | 15/85 | 68 | 4,293 | 91.8 | Clear |
| 11 | 1/99 | 68 | 4,256 | 91.0 | Slight Haze |
| 12 | 1/99 | 68 | 4,209 | 90.0 | Slight Haze |
| 13 | 1/99 | 68 | 4,214 | 90.1 | Slight Haze |
| 14 | 1/99 | 68 | 4,198 | 90.0 | Slight Haze |
| 15 | 1/99 | 68 | 4,268 | 91.4 | Slight Haze |
| 16 | 50/50 | 68 | 4,149 | 88.8 | Clear |
| 17 | 50/50 | 68 | 4,208 | 90.0 | Clear |
| 18 | 50/50 | 68 | 4,227 | 90.4 | Clear |
| 19 | 50/50 | 68 | 4,168 | 89.2 | Clear |
| 20 | 50/50 | 68 | 4,190 | 90.0 | Clear |
| 21 | 34/66 | 81 | 4,194 | 89.7 | Clear |
| 22 | 34/66 | 99 | 4,174 | 89.3 | Clear |
| 23 | 34/66 | 111 | 4,077 | 87.2 | Clear |

The reaction solvent used in each experiment was as follows:
Batches 1–20: hexane
Batch 21: cyclohexane
Batch 22: heptane
Batch 23: toluene The results demonstrate that high yields of high purity butyllithium product are obtained by reaction of the sodium:lithium alloy with butyl chloride, with the reaction taking place under reflux conditions. Clear, colorless products were obtained when the ratio of sodium to lithium was greater than 1:99 and less than 50:50. The reaction time for each reaction was approximately 70 minutes.

What is claimed is:

1. A process for producing alkyllithium compounds in high yields of at least about 90% and high purity by reacting under reflux conditions in a liquid hydrocarbon solvent which refluxes at temperatures between about 50° C. and 125° C., such solvent being selected from liquid saturated aliphatic hydrocarbons containing 5 to 12 carbon atoms, saturated liquid cycloaliphatic hydrocarbons containing 5 to 12 carbon atoms and liquid aromatic hydrocarbons containing 6 to 12 carbon atoms and mixtures thereof, an alkyl halide containing 3 to 16 carbon atoms with metal particles of less than about 300 microns in size, and subsequently recovering the alkyllithium compound, in which the improvement consists of conducting the reaction using metal particles of a lithium-sodium alloy which comprises at least about 15 percent by weight of sodium.

2. The process of claim 1, wherein the lithium-sodium alloy comprises about 34% by weight sodium and about 66% by weight lithium.

3. The process of claim 1, wherein the alkyl halide is an alkyl chloride containing from about 3 to about 16 carbon atoms.

4. The process of claim 1, wherein the alkyl halide is butyl chloride.

5. The process of claim 1, wherein the solvent is hexane and the reaction temperature is between about 68–80° C.

6. The process of claim 1, wherein the solvent is heptane and the reaction temperature is between about 99–110° C.

7. The process of claim 1, wherein the solvent is cyclohexane and the reaction temperature is between about 80–90° C.

8. The process of claim 1, wherein the solvent is toluene and the reaction temperature is between about 110–120° C.

9. The process of claim 1, wherein the reaction time is about 70 minutes.

10. The process of claim 5, wherein the alkyl halide is an alkyl chloride containing from 3 to 16 carbon atoms.

11. The process of claim 10, wherein the alkyl halide is butyl chloride.

12. The process of claim 6, wherein the alkyl halide is an alkyl chloride containing from 3 to 16 carbon atoms.

13. The process of claim 12, wherein the alkyl halide is butyl chloride.

14. The process of claim 7, wherein the alkyl halide is an alkyl chloride containing from 3 to 6 carbon atoms.

15. The process of claim 14, wherein the alkyl halide is butyl chloride.

16. The process of claim 8, wherein the alkyl halide is an alkyl chloride containing from 3 to 16 carbon atoms.

17. The process of claim 16, wherein the alkyl halide is butyl chloride.

18. The process of claim 9, wherein the alkyl halide is an alkyl chloride containing from 3 to 16 carbon atoms.

19. The process of claim 18, wherein the alkyl halide is butyl chloride.

* * * * *